United States Patent [19]

Roberts et al.

[11] 4,413,118
[45] Nov. 1, 1983

[54] PROCESS FOR REMOVAL OF HOMOGENEOUS CATALYST GROUP VIII METALS FROM PROCESS STREAMS

[75] Inventors: F. Edward Roberts, Princeton; Victor J. Grenda, Warren, both of N.J.

[73] Assignee: Merck & Co., Inc., Rahway, N.J.

[21] Appl. No.: 239,726

[22] Filed: Mar. 2, 1981

[51] Int. Cl.$^3$ .............................................. C07H 17/08
[52] U.S. Cl. ................................... 536/7.1; 585/269; 585/270; 585/273; 585/274; 585/509; 568/881; 562/606; 560/231
[58] Field of Search .............. 536/17 C, 7.1; 585/269, 585/270, 273, 274, 509; 560/231; 562/606; 568/881

[56] References Cited

U.S. PATENT DOCUMENTS 4,199,569  4/1980  Chabala et al. ..................... 536/7.1

OTHER PUBLICATIONS

Chemical Abstracts 87: 21051p; (1977) Shome et al.
Chemical Abstracts 87: 207296t (1977) Petrukhin et al.
Chemical Abstracts 87: 26574m (1977) French Patent 2,305,398.
Chemical Abstracts 85: 198752t (1976) Ludwig et al.
Chemical Abstracts 85: 167394y (1976) Ivanova et al.
Chemical Abstracts 85: 116223j (1976) Radushev et al.
Chemical Abstracts 85: 5888k (1976) Onoda et al.
Chemical Abstracts 85: 69021j (1976) Rakovskii et al.
Chemical Abstracts 81: 57815w (1974) Shlenskaya et al.
Chemical Abstracts 79: 73174a (1973) Diamantatos et al.
Chemical Abstracts 76: 18515a (1972) Chizh et al.
Chemical Abstracts 52: 18084c (1958) Usova et al.
*Chemical Abstracts*, 88, 181886d to Murti et al. (1978).
*Chemical Abstracts*, 91, 32361p to Uttarwar et al. (1979).
*Chemical Abstracts*, 89, 190380g to Das et al. (1978).
*Chemical Abstracts*, 86, 143468v to Barkan (1977).

*Primary Examiner*—Nicky Chan
*Attorney, Agent, or Firm*—David L. Rose; Mario A. Monaco

[57] ABSTRACT

Organic sulfur compounds containing a carbon-sulfur double bond are used to remove homogeneous catalyst group VIII metals from chemical process streams.

6 Claims, No Drawings

PROCESS FOR REMOVAL OF HOMOGENEOUS CATALYST GROUP VIII METALS FROM PROCESS STREAMS

BACKGROUND OF THE INVENTION

This invention is concerned with a novel process for removing homogeneous catalyst group VIII metals from chemical process streams which comprises treating the process streams with organic sulfur compounds containing a carbon-sulfur double bond.

Homogeneous catalysts containing group VIII metals, such as Wilkinson's catalyst, chloro tris triphenylphosphine rhodium, RhCl(P∅$_3$)$_3$, are commercially important in the chemical industry. Because of their inherent cost, it is economically important that as much of the metal as possible be easily recoverable without loss of product yield. It is also important, particularly in the pharmaceutical industry, that the products not be contaminated with the metal.

Heretofore, recovery of metals from homogeneous catalysts has involved ionic species or conversion to ionic species by oxidation such as with nitric acid and hydrogen peroxide. Also, polymeric sulfur containing resins have been used but these suffer from the disadvantage of being expensive and the need to prepare the resins as well as the need to recover the metal from the resin.

Other methods of recovery such as adsorption on activated carbon, silica gel or alumina present difficult, expensive recovery problems in that the metal is present in very low concentrations, usually measured in parts per million, and that the adsorbent is difficult to get rid of.

Furthermore, most of the known methods for recovery of homogeneous catalyst metals deal with recovery after the desired product has been removed by some prior isolation steps such as distillation, filtration and the like at which point the metal may be distributed among various filter cakes, filtrates and the like depending on the isolation procedures. None of the known methods is suitable for treating process streams still containing the desired product.

Now, with the present invention there is provided a novel process for removing homogeneous catalyst group VIII metals from chemical process streams which comprises treating the process streams with an organic sulfur compound containing a carbon-sulfur double bond, preferably, thiourea.

It is an advantage of the novel process that recovery of the metal can occur before the desired product is isolated and before the metal is dispersed among various fractions of the original process stream.

It is a further advantage of the novel process that the metal is recovered in high concentration. The organic sulfur compound/metal complex often contains the metal in higher concentration that did the original homogeneous catalyst.

DETAILED DESCRIPTION OF THE INVENTION

This invention is concerned with a novel process for removing homogeneous catalyst group VIII metals from chemical process streams which comprises treating the process streams with an organic sulfur compound containing a carbon-sulfur double bond.

The metals with which the novel process of this invention is operable are those generally known as group VIII and sometimes as the platinum group and includes such as: rhodium, which is used in certain hydrogenations, or hydrogenolyses in the form of Wilkinsons's catalyst, chloro tris(triphenylphosphine)rhodium (I), RhCl(P∅$_3$)$_3$, which is used herein to illustrate the novel process of this invention; or hydridocarbonyltris (triphenylphosphine)rhodium (I), HRh(CO)(P∅$_3$)$_3$; iridium, as IrH$_3$(P∅$_3$)$_3$ used for reducing aldehydes (J. Chem. Soc., A (1969) 1961) and reducing activated olefins such as acrylic acid or its esters, (Chem. Comm., (1967) 923), or as IrH(CO)(P∅$_3$)$_3$ used for reducing acetylenes to ethylenes (Inorg. Nucl. Chem. Lett., 4 687(1968)); palladium as PdCl$_2$(P∅$_3$)$_2$ used for coupling zinc acetylides with arylhalides (J. Org. Chem., 43, 358 (1978)); and nickel as Br$_2$Ni(P∅$_3$)$_2$ or naphthyl BrNi(P∅$_3$)$_2$ used in Stereospecific alkenyl-alkenyl cross coupling (J. Amer. Chem. Soc., 98, 6729 (1976)).

The organic sulfur compounds containing a carbon-sulfur double bond which are useful in the novel process of this invention form complexes with the group VIII metals which complexes are insoluble in the process streams, are themselves easily recoverable from the process streams by virtue of their insolubility or extractability and include such as N-benzyldithiocarbamoylglycine, β-dithiocarbamylpropionic acid, thiohydantoin, thiourea, ammonium dithiocarbamate, thiobarbituric acid, thiosemicarbazide, rhodamine, and 2-mercapto-4-aminopyrimidine. The preferred organic sulfur compounds are thiourea and thiohydantoin, especially thiourea.

The process stream solvent must be an inert organic solvent in which the organic sulfur compound and the complex with the metal are relatively insoluble at ice-bath temperature, such as benzene, toluene, o, m, or p-xylene, tetrahydrofuran, methylene chloride or the like.

The novel process comprises heating the process stream containing the homogeneous catalyst with about 2 to about 12 moles, preferably about 5 moles, or organic sulfur compound per mole of group VIII metal with agitation at 50°–100° C. for about 2 to about 10 hours, preferably about 3–6 hours followed by cooling to about 0°–5° C. followed by filtration, and if necessary, by extraction with a weakly basic aqueous solution, preferably a sodium carbonate solution.

The novel process of the present invention is well illustrated by reference to the process for preparing ivermectin, which is a known compound which has significant parasiticidal activity as an anthelmintic, ectoparasiticide, insecticide and acaricide, in human and animal health and in agriculture. Chabala et al., U.S. Pat. No. 4,199,569. The process for its preparation described therein is as follows:

Ivermectin

22,23-Dihydro Avermectin B1a 39 g of Avermectin B1a is dissolved in 1540 ml of toluene and introduced into a 4 liter stirred autoclave. To this is added 3.9 g of tris(triphenylphosphine)rhodium (I) chloride (Wilkinson's catalyst). A hydrogenation pressure of 40 psi and a temperature of 40° C. is maintained with stirring for 4½ hours. At the end of this period liquid chromatographic analysis indicates 98% yield of dihydro avermectin B1a with 1.5% of tetrahydro avermectin B1a. The toluene is removed by evaporation in vacuo and the dark red gum is dissolved in ethanol at a rate of 4 ml of ethanol per gram of product.

Formamide at a rate of 10 ml per gram of product is added and the solution heated on the steam bath to 40°–50° while adding water at a rate of 2 ml per gram of product. After crystallization commences the heat is removed and the solution allowed to cool slowly with stirring overnight. The solid is filtered off and washed with a mixture 3 parts water and 1 part ethanol and dried in vacuo overnight. The solids are dissolved in 150 ml of ethanol and warmed to 35°–40° C. on the steam bath. Water, 150 ml is added slowly with stirring. When solution is complete at 35° C. the heat is removed and the solution allowed to cool slowly overnight. The crystals are removed by filtration and washed with aqueous ethanol and dried in vacuo overnight affording 32.55 g of 22,23-dihydro avermectin Bla with a m.p. of 155°–157° C.

Following operation of that process about 85% of the Wilkinson's catalyst charged is accounted for in the various mother liquors and washes. Up to 15% (100–200 ppm rhodium as determined by atomic absorption) is present in the final product. This loss of rhodium effects overall catalyst recovery and the presence of the catalyst in different mother liquor streams makes recovery difficult.

The process, as modified by the present invention is as follows:

EXAMPLE 1

| Materials: | |
|---|---|
| Dry toluene solution of avermectin $B_1$ | 100 ml |
| containing | 17.2 g (LC assay basis) |
| Wilkinson's catalyst [chloro tris triphenyl phosphine rhodium (I)] | 198 mg |
| Thiourea | 76 mg |

The toluene solution was charged to a 300 ml stirred autoclave containing 193 mg Wilkinson's catalyst. The autoclave was purged of oxygen by alternately pressurizing with nitrogen, then lowering the pressure by vacuum, three times. The autoclave was pressurized to 40 psi hydrogen and the temperature raised to 40°. The reaction was sampled by means of a sampling blow leg and the course of reaction followed by LC assay. After 4½ hours, the level of $B_{1a}$ remaining had dropped to less than 0.3% so the reaction was stopped. The dark red-brown toluene solution was transferred to a 250 ml round bottom flask fitted with a stirrer, thermometer and nitrogen inlet. Thiourea, 76 mg, was added and the mixture was heated to 95° (internal temperature) while maintaining a nitrogen atmosphere. The internal temperature was maintained at 95° for 5 hours. At the end of the age period, the mixture was cooled to 0°–5° and aged for 30 minutes.

The red-brown precipitate was collected on a sintered glass funnel and washed with 2×5 ml toluene. The toluene solution (light yellow) was carried forward and the ivermectin was isolated and recrystallized essentially as described in the process of U.S. Pat. No. 4,199,569 included above.

A material balance relative to rhodium as determined by atomic absorption spectroscopy, is 97–98% with 94% of the rhodium being accounted for in the thiourea complex filter cake. Table I shows the distribution of rhodium in the process streams.

TABLE I

| Rhodium Distribution in Ivermectin Process Streams | |
|---|---|
| Source | % Rh charged |
| Toluene solution at the end of hydrogenation | 100% |
| Thiourea filter cake | 94% |
| Toluene filtrate after thiourea treatment | 3% |
| crude mother liquor | 2.6% |
| pure mother liquor | 0.3% |
| Ivermectin (final product) | 0.7% (10 ppm) |
| Rhodium material balance | 97.8% |

EXAMPLE 2

Determination of Optimum Conditions

Optimum conditions for removal of rhodium with thiourea were determined by a series of probe experiments as follows:

A toluene solution of Wilkinson's catalyst was treated with 12 moles of thiourea/mole catalyst and heated at 100° C. for 1, 3 and 5 hours. After cooling at 0°–5° C. for 30 minutes the precipitate was collected and the toluene solution assayed for rhodium by atomic absorption. The amount of rhodium removed was 90, 93 and 96% respectively.

Similar experiments employing 2, 5 and 12 moles of thiourea/mole of catalyst for 5 hours at 100° C. gave 22, 95 and 95% rhodium removal respectively.

Optimum conditions were thus determined to be about 5 moles of thiourea/mole of catalyst for 5 hours.

EXAMPLE 3

Utility with Other Catalysts

Employing probe experiments as described in Example 2 with the optimum conditions determined therein, but substituting the various catalysts shown in Table II for the Wilkinson's catalyst, the efficiency of recovery is as shown.

TABLE II

| Catalyst | % Catalyst Removed |
|---|---|
| $IrH_3(P\phi_3)_3$ | 87% |
| $IrH(CO)P\phi_3)_3$ | 93% |
| $PdCl_2(P\phi_3)_2$ | 100% |
| Naphthyl $BrNi(P\phi_3)_2$ | 100% |
| $Br_2Ni(P\phi_3)_2$ | 96% |

EXAMPLE 4

Utility of Organic Sulfur Compounds

Employing the procedure of Example 2 and the optimum conditions described therein but employing the sulfur compounds described in Table III there is recovered the amount of rhodium also shown in Table III by the indicated process.

TABLE III

| Structure | Method of Removal | % Rh Removal |
|---|---|---|
| ⟨O⟩—CH$_2$—S—C(=S)—NHCH$_2$CO$_2$H<br>N—benzyldithio-carbamoylglycine | Filter solid + extraction with NaHCO$_3$ | 92 |

TABLE III-continued

| Structure | Method of Removal | % Rh Removal |
|---|---|---|
| $NH_2-\overset{\overset{S}{\|}}{C}-S-(CH_2)_2-CO_2H$ <br> β-dithiocarbamyl-propionic acid | Filter solid + extraction with NaHCO$_3$ | 78 |
| thiohydantoin | Filter solid + extraction with NaHCO$_3$ | 95 |
| $NH_2-\overset{\overset{S}{\|}}{C}-NH_2$ <br> thiourea | Filter ppt. | 95 |
| $NH_4{}^+-S-\overset{\overset{S}{\|}}{C}-NH_2$ <br> ammonium dithiocarbamate | Aqueous solution contacted with organic solvent | 63 |
| thiobarbituric acid | Extraction with NaHCO$_3$ | 79 |
| $NH_2-\overset{\overset{S}{\|}}{C}-NH-NH_2$ <br> thiosemicarbazide | Aqueous solution contacted with organic solvent | 32 |
| rhodamine | Aqueous solution contacted with organic solvent | 32 |
| 2-mercapto-4-aminopyrimidine | Filter ppt. | 31 |

What is claimed is:

1. A process for removing homogenous triphenylphosphine substituted Group XIII metal catalysts selected from RhCl(Pϕ$_3$)$_3$, IrH$_3$(Pϕ$_3$)$_3$, IrH(CO)(Pϕ$_3$)$_3$, PdCl$_2$(Pϕ$_3$)$_2$, naphthyl BrNi(Pϕ$_3$)$_2$, Br$_2$Ni(Pϕ$_3$)$_2$ from toluene solvent-containing reaction process streams, which comprises adding about 2 to about 12 moles of an organic sulfur compound containing a carbon sulfur double bond selected from N-benzyl-dithiocarbamoylglycine, β-dithiocarbamylpropionic acid, thiohydantoin, thiourea, ammonium dithiocarbamate, thiobarbituric acid, thiosemicarbazide, rhodamine or 2-mercapto-4-aminopyrimidine, per mole of said Group VIII metal, warming to 50° to 100° C. for from 2 to 10 hours, cooling to 0° to 5° C. and separating the metal-organic sulfur complex that forms.

2. In a process for preparing ivermectin which comprises the steps of:
 (a) hydrogenating avermectin B1a in the presence of tris-(triphenylphosphine)rhodium (I) chloride in an organic solvent selected from benzene, toluene, o-, m- or p-xylene, tetrahydrofuran and methylene chloride;
 (b) evaporating the organic solvent;
 (c) dissolving the residue in ethanol;
 (d) treating the ethanol solution with formamide and water to cause crystallization of the product;
 wherein the improvement comprises after the hydrogenation step (a) and before the evaporation step (b), adding about 2 to about 12 moles of an organic sulfur compound containing a carbon sulfur double bond selected from the group consisting of N-benzyldithiocarbamoylglycine, β-dithiocarbamylproprionic acid, thiohydantoin, thiourea, ammonium dithiocarbamate, thiobarbituric acid, thiosemicarbazide, rhodamine or 2-mercapto-4-aminopyrimidine, per mole of tris-(triphenylphosphine)rhodium (I) chloride; warming to 50° to 100° C. for from 2 to 10 hours; cooling to 0° to 5° C. and separating the rhodium-organic sulfur complex that forms.

3. The process of claim 1, wherein the organic sulfur compound is thiourea or thiohydantoin.

4. The process of claim 3 wherein the organic sulfur compound is thiourea.

5. The improved process of claim 2 wherein the organic sulfur compound is thiourea or thiohydantoin.

6. The improved process of claim 5 wherein the organic sulfur compound is thiourea.

* * * * *